United States Patent
Rudolf et al.

(10) Patent No.: US 11,958,823 B2
(45) Date of Patent: *Apr. 16, 2024

(54) PROCESS FOR THE MANUFACTURING OF A POLYMER WITH URETHANE GROUPS

(71) Applicant: BASF SE, Ludwigshafen am Rhein (DE)

(72) Inventors: Peter Rudolf, Ludwigshafen (DE); Indre Thiel, Ludwigshafen (DE); Hans-Josef Thomas, Ludwigshafen (DE); Hannes Blattmann, Cologne (DE)

(73) Assignee: BASF SE, Ludwigshafen am Rhein (DE)

( * ) Notice: Subject to any disclaimer, the term of this patent is extended or adjusted under 35 U.S.C. 154(b) by 10 days.

This patent is subject to a terminal disclaimer.

(21) Appl. No.: 16/639,339

(22) PCT Filed: Aug. 7, 2018

(86) PCT No.: PCT/EP2018/071335
§ 371 (c)(1),
(2) Date: Feb. 14, 2020

(87) PCT Pub. No.: WO2019/034470
PCT Pub. Date: Feb. 21, 2019

(65) Prior Publication Data
US 2020/0354333 A1   Nov. 12, 2020

(30) Foreign Application Priority Data

Aug. 17, 2017 (EP) .................................... 17186543

(51) Int. Cl.
C07D 327/04 (2006.01)
C08G 71/04 (2006.01)

(52) U.S. Cl.
CPC .......... C07D 327/04 (2013.01); C08G 71/04 (2013.01)

(58) Field of Classification Search
None
See application file for complete search history.

(56) References Cited

U.S. PATENT DOCUMENTS

| | | |
|---|---|---|
| 2,828,318 A | 3/1958 | Reynolds |
| 3,072,676 A | 1/1963 | Johnson et al. |
| 3,201,416 A | 8/1965 | Johnson et al. |
| 3,232,936 A | 2/1966 | Reynolds |
| 3,349,100 A | 10/1967 | Villa |
| 3,517,029 A | 1/1970 | Johnson |
| 6,372,871 B1 | 4/2002 | Jimbo et al. |
| 2016/0122473 A1 | 5/2016 | Monnier et al. |
| 2020/0239633 A1* | 7/2020 | Rudolf ................ C08G 71/04 |
| 2021/0171811 A1 | 6/2021 | Licht et al. |
| 2022/0127241 A1 | 4/2022 | Rudolf et al. |

FOREIGN PATENT DOCUMENTS

| | | | |
|---|---|---|---|
| EP | 0 279 303 A2 | 8/1988 | |
| EP | 1334965 | 8/2003 | |
| EP | 1 506 964 A1 | 2/2005 | |
| EP | 2 468 791 A1 | 6/2012 | |
| EP | 2468791 A1 * | 6/2012 | ......... C08G 59/4064 |
| JP | H04-264075 | 9/1992 | |
| JP | 2007178903 A * | 7/2007 | |
| WO | WO 2011/157671 A1 | 12/2011 | |
| WO | WO 2013/144299 A1 | 10/2013 | |
| WO | WO 2014/188116 A1 | 11/2014 | |

OTHER PUBLICATIONS

Libretexts Chemistry, "Aliphatic hydrocarbons," pp. 1-17, (2023) https://chem.libretexts.org/Bookshelves/Introductory_Chemistry/Chemistry_for_Changing_Times_(Hill_and_McCreary)/09%3A_Organic_Chemistry/9.02%3A_Aliphatic_Hydrocarbons (Year: 2023).*
International Search Report dated Nov. 6, 2018 in PCT/EP2018/071335, 4 pages.
International Preliminary Report on Patentability and Written Opinion of the International Searching Authority issued on Feb. 18, 2020 in PCT/EP2018/071335 filed Aug. 7, 2018, 8 pages.
M. Luo, et al., "Synthesis of Cyclic Monothiocarbonates via the Coupling Reaction of Carbonyl Sulfide (COS) with Epoxides" Catalysis Science & Technology, vol. 6, No. 1, XP055518365, Jan. 1, 2016, pp. 188-192.
Richard C. Forster, et al., "Dithiols. Part 28. Conversion of 1,3-Dithiolan-2-Ones, 1,3-Oxathiolan-2-Ones and 1,3-Oxathiolan-2-Thiones into 1,3-Dithiolan-2-Thiones" Journal of the Chemical Society, Perkin I, Transactions 1, Issue 8, XP055518366, Jan. 1, 1978, pp. 822-829.
Nobuhiro Kihara, et al., "Preparation of 1,3-Oxathiolane-2-thiones by the Reaction of Oxirane and Carbon Disulfide" Journal of Organic Chemistry, vol. 60, No. 2, Jan. 1, 1995, pp. 473-475.
D. D. Reynolds, et al., "Mercaptoethylation. II. Preparation of 2-Mercaptoethyl Carbamates and Oligoethylene Sulfides" Journal of Organic Chemistry, vol. 26, Issue 12, Dec. 1, 1961, pp. 5111-5115.

(Continued)

Primary Examiner — Randy P Gulakowski
Assistant Examiner — Ha S Nguyen
(74) Attorney, Agent, or Firm — Grüneberg and Myers PLLC

(57) ABSTRACT

Object of the invention is a process for the manufacturing of a polymer with urethane groups, wherein in a first alternative A) a five-membered cyclic monothiocarbonate B) a compound with at least two amino groups, selected from primary or secondary amino groups, and C) a compound which at least two functional groups that react with a group —SH or, in case of a carbon-carbon triple bond as functional group that react with a group —SH, a compound with at least one carbon-carbon triple bond are reacted or wherein in a second alternative A) a five-membered cyclic monothiocarbonate and D) a compound with at least one primary or secondary amino group and at least one functional group that reacts with a group —SH.

20 Claims, No Drawings

(56) References Cited

OTHER PUBLICATIONS

Yi-Ming Wang, et al., "Cooperative Catalysis with Binary Lewis Acid—Lewis Base System for the Coupling of Carbon Disulfide and Epoxides" Applied Organometallic Chemistry, vol. 26, Issue 11, Sep. 20, 2012, pp. 614-618.
U.S. Appl. No. 16/633,870, filed Jan. 24, 2020, Peter Rudolf, et al.
U.S. Appl. No. 16/634,230, filed Jan. 27, 2020, Peter Rudolf, et al.
U.S. Appl. No. 16/639,204, filed Feb. 14, 2020, Peter Rudolf, et al.
Etlis et al., "Reaction of Chloro Derivatives of Alkene Thiocarbonates with Ammonia and Amines", Doklady Akademii Nauk SSSR, vol. 142, No. 4, 1962, with English translation, 7 pages.
Goethals et al., "Diversely Substituted Polyamide Structures through Thiol-Ene Polymerization of Renewable Thiolactone Building Blocks", Macromolecules, vol. 47, 2014, pp. 61-69.
Jerry March, Advanced Organic Chemistry, Reactions, Mechanisms, and Structure, $4^{th}$ Edition, 1992, pp. 766-767.
Pen-Chung Wang, "A new synthesis of 2-Oxathiolone", Heterocycles, vol. 24, No. 2, 1986, pp. 329-330.
Rangelov et al., "Towards the synthesis of amino-substituted epoxides: synthesis and characterization of glycidyldidodecylamine", Designed Monomers and Polymers, vol. 4, No. 1, 2001, pp. 39-43.
U.S. Office Action dated Jul. 20, 2023, in U.S. Appl. No. 17/646,766, 19 pages.
U.S. Appl. No. 17/646,766, filed Jan. 3, 2022, 2022/0127241, Rudolf et al.
Bingham et al., "Thiocarbonyl chemistry in polymer science", Polymer Chemistry, vol. 13, 2022, pp. 2880-2901.
Calo et al., "Cyclic Carbonate Formation from Carbon Dioxide and Oxiranes in Tetrabutylammonium Halides as Solvents and Catalysts", Organic Letters, vol. 4, No. 15, 2002 pp. 2561-2563.
Fan et al. "Adaptable Strategy to Fabricate Self-Healable and Reprocessable Poly(thiourethane-urethane) Elastomers via Reversible Thiol-Isocyanate Click Chemistry", Macromolecules, vol. 53, 2020, pp. 4284-4293.
Friederichs et al., "Determination of Dithiocarbamate residues in Dietetic Foods (e.g. Ready-to-Eat Baby Food)", Application GC-6, SCA-180-006, Shimadzu Europa GmbH, Mar. 1993, 4 pages.
Kihara et al., "Catalytic Activity of Various Salts in the Reaction of 2,3-Epoxypropyl Phenyl Ether and Carbon Dioxide under Atmospheric Pressure", J. Org. Chem., vol. 58, 1993, pp. 6198-6202.
Levinn et al., "Development and Application of Carbonyl Sulfide-Based Donors for $H_2S$ Delivery", Accounts of Chemical Research, vol. 52, 2019, pp. 2723-2731.
Taguchi et al., "The Synthesis of 1,3-Dithiolan-2-ones on the Reaction of Oxiranes with Carbon Disulfide under High Pressure", Bull. Chem. Soc, Jpn., vol. 62, No. 2, 1989, pp. 474-478.
Tomita et al., "Polyaddition of Bis(cyclic thiocarbonate) with Diamines. Novel Efficient Synthetic Method of Polyhydroxythiourethanes", Macromolecules, vol. 34, 2001, pp. 727-733.
Zhao et al., "Kinetic Insights into Hydrogen Sulfide ($H_2S$) Delivery from Caged-Carbonyl Sulfide (COS) Isomeric Donor Platforms", J. Am. Chem. Soc., vol. 139, No. 45, Nov. 15, 2017, 30 pages.
U.S. Office Action dated Sep. 27, 2023, in U.S. Appl. No. 17/257,749, 21 pages.
U.S. Appl. No. 17/257,749, filed Jan. 4, 2021, 2021/0171811, Licht et al.
U.S. Office Action dated Jan. 23, 2024, in U.S. Appl. No. 17/646,766, 17 pages.

* cited by examiner

PROCESS FOR THE MANUFACTURING OF A POLYMER WITH URETHANE GROUPS

Object of the invention is a process for the manufacturing of a polymer with urethane groups, wherein in a first alternative
A) a five-membered cyclic monothiocarbonate
B) a compound with at least two amino groups, selected from primary or secondary amino groups, and
C) a compound which at least two functional groups that react with a group —SH or, in case of a carbon-carbon triple bond as functional group that react with a group —SH, a compound with at least one carbon-carbon triple bond
are reacted or wherein in a second alternative
A) a five-membered cyclic monothiocarbonate and
D) a compound with at least one primary or secondary amino group and at least one functional group that reacts with a group —SH
are reacted.

Polyurethanes are important industrial polymers. They have very good mechanical properties and are therefore used in many technical applications. They are used, for example, as or in thermoplastics, foams or coatings. Polyurethanes are usually prepared by reacting compounds with isocyanate groups, notably di- and polyisocyanates, with diols and/or polyols. Compounds with isocyanate group are usually highly reactive. Such reactivity leads to increased moisture sensitivity which is problematic in some technical applications. Some compounds with isocyanate groups are considered to be harmful and may cause allergies in case of skin contact or inhalation.

There is a demand to find alternative processes for the manufacturing of polyurethanes thus avoiding the use of compounds with isocyanate groups.

WO 2013/144299 discloses radically polymerizable compounds with a cyclic five membered carbonate ring system (alkylidene-1,3-dioxolan-2-one). Urethane groups are formed by reacting these compounds or polymers thereof with amino compounds. Similar compound are disclosed in WO 2011/157671 for the use as reactive diluents in epoxy resins. However, the synthesis of such compounds is tedious. Necessary precursors of the synthesis are not commercially available.

From EP-A 1506964 and U.S. Pat. No. 6,372,871 cyclic dithiocarbonates are known. Thiourethane groups (—NH—(C=S)—O) are obtained by reacting cyclic dithiocarbonates with amines. Polythiourethans are not a suitable substitute for polyurethanes.

The object of EP-A 2468791 are epoxy compositions that comprise compounds with five membered cyclic ring system comprising oxygen and sulfur. The compounds used in EP-A 2468791 are dithiocarbonates. J. Org. Chem. 1995, 60, 473 to 475 which is cited in EP-A 2468791 discloses dithiocarbonates, only.

D. D. Reynolds, D. L. Fields and D. L. Johnson. JOC, 26, 1961, page 5111 to 5115, disclose compounds with a five-membered cyclic thiocarbonate ring system and reactions thereof. Inter alia a reaction with an amino compound is mentioned.

M. Luo, X.-H. Zhang and D. J. Darensbourg, Catalysis Science & Technology, 2015, article accepted on 13 Aug. 2015 (DOI: 10.1039/c5cy00977d) disclose some specific cyclic monothiocarbonates obtained via coupling reaction of carbonyl sulfides with epoxides.

Yi-Ming Wang, Bo Li, Hui Wang, Zhi-Chao Zhang and Xiao-Bing Lu, Appl. Organometal. Chem. 2012, 26, 614-618 also disclose some specific cyclic monothiocarbonates obtained via coupling reaction of carbonyl sulfides with epoxides.

It was an object of this invention to provide an alternative method for the manufacturing of polymers with urethane groups and to avoid the use of compounds with isocyanate groups. Furthermore, it was an object of this invention to provide hybrid polymers that comprise urethane groups, for example hybrid polymers based on epoxy resins. The polymers should be obtainable by an easy and effective manufacturing process which includes moderate temperatures, the lack of condensation by products as, for example, water or alcohol and the absence or at least reduced amount of solvents. The obtained polymers should have satisfying or even improved properties, such properties are, for example, mechanical properties, optical properties, stabilities as UV and corrosion protection. There is also an interest in polymers that have functional groups that easily undergo chemical reactions, thus allowing easy modification or crosslinking of the polymers.

Accordingly, the process described above and polymers obtainable by the process have been found.

To the monothiocarbonate A)

The five-membered cyclic monothiocarbonate A) is a compound with one five-membered cyclic monothiocarbonate group. A five-membered cyclic monothiocarbonate group is a ring system with 5 members, three of them are from the monothiocarbonate —O—C(=O)—S— and the further two members are carbon atoms closing the five-membered cycle.

The monothiocarbonate may comprise further heteroatoms such as oxygen, sulfur, nitrogen or chloride or silicium, for example in form of functional groups selected from an epoxy group, an ether group, a hydroxy group, a keto or aldehyde or ester group, a hydroxyl group, a carboxy group, a thioether or a thiol group, or tertiary amino group or silicium functional groups. In a preferred embodiment, the monothiocarbonate has at maximum one further functional group besides the monothiocarbonate group.

The monothiocarbonate may have a molecular weight of from 104 g/mol to, for example, 100.000. The latter might be the case if the monothiocarbonate is a high molecular compound such as a polymer comprising one monothiocarbonate group, only. Preferred monothiocarbonates have a molecular weight of from 104 g/mol to 5000 g/mol. More preferred are monothiocarbonates having a molecular weight of from 104 g/mol to 1000 g/mol and most preferred are monothiocarbonates having a molecular weight of from 104 g/mol to 500 g/mol.

In a preferred embodiment compounds A) do not comprise any primary or secondary amino groups and do not comprise any functional groups which react with the group —SH as listed for compound C).

In a particularly preferred embodiment compounds A) do not comprise other functional groups than monothiocarbonate groups, carboxylic ester groups or ether groups.

Preferred are monothiocarbonates of formula I

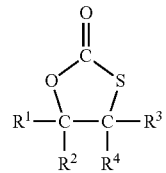

with $R^1$ to $R^4$ independently from each other representing hydrogen or an organic group with up to 50 carbon atoms whereby, alternatively, $R^2$, $R^4$ and the two carbon atoms of the thiocarbonate group may also together form a five to ten membered carbon ring In case that any of $R^1$ to $R^4$ represent an organic group, such organic group is preferably an organic group with up to 30, more preferably up to 20 carbon atoms carbon atoms. In a further preferred embodiment $R^2$ and $R^4$ do not form a five to ten membered carbon ring together with the two carbon atoms of the thiocarbonate group.

In case that any of $R^1$ to $R^4$ represent an organic group, such organic group may comprise heteroatoms and functional groups as listed above. In particular, it may comprise oxygen, nitrogen, sulfur, silicon and chloride. In a preferred embodiment, the organic group may comprise oxygen or chloride. $R^1$ to $R^4$ may comprise oxygen for example in form of ether, hydroxy, aldehyde, keto or carboxy groups. In a preferred embodiment, the organic group is an aliphatic organic group with up to 30 carbon atoms which may comprise oxygen, nitrogen or chloride, in particular oxygen.

In a more preferred embodiment, the organic group is selected from an alkyl group, from a group $—CH_2—O—R^5$ or a group $—CH_2—O—C(=O)—R^6$ or a group $—CH_2—NR^7R^8$ with $R^5$ to $R^8$ being an organic group with up to 30 carbon atoms, preferably up to 20 carbon atoms. In particular, $R^5$ to $R^8$ represent an aliphatic or aromatic group, which may comprise oxygen, for example in form of ether groups. In a preferred embodiment, $R^5$ to $R^8$ represent an aliphatic hydrocarbon group, such as an alkyl group with 1 to 10 carbon atoms, an alkoxy group or a poly-alkoxy group. In a most preferred embodiment, $R^5$ to $R^8$ represent an aliphatic hydrocarbon group, in particular an alkyl group with 1 to 10 carbon atoms.

In a most preferred embodiment, the organic group is a group $—CH_2—O—R^5$ or a group $—CH_2—O—C(=O)—R^6$.

Preferably, two to all four of $R^1$ to $R^4$ in formula I represent hydrogen and the remaining groups $R^1$ to $R^4$ represent an organic group.

More preferably, two or three of $R^1$ to $R^4$ in formula I represent hydrogen and the remaining groups $R^1$ to $R^4$ represent an organic group.

Most preferably, three of $R^1$ to $R^4$ in formula I represent hydrogen and the remaining group of $R^1$ to $R^4$ represents an organic group. In a preferred embodiment $R^1$ or $R^2$ is the remaining group representing an organic group. Most preferably $R^1$ is the remaining group representing an organic group.

A particularly preferred compound of formula I is a compound wherein $R^2$ to $R^4$ in formula I represent hydrogen and $R^1$ is a group $—CH_2—O—R^5$ or a group $—CH_2—O—C(=O)—R^6$ or a group $—CH_2—NR^7R^8$ with $R^5$ to $R^8$ being an C1 to C14 alkyl group, preferably a C4 to C14 alkyl group.

As preferred monothiocarbonates may be mentioned:

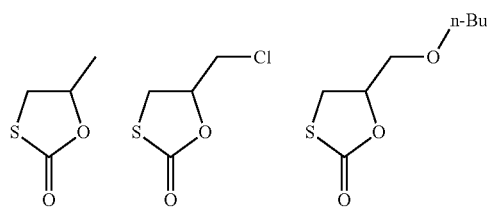

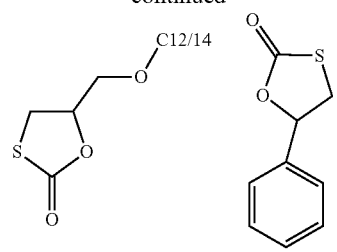

To the synthesis of monothiocarbonate A)

Some methods for the synthesis of monothiocarbonates are described in the state of the art.

According to U.S. Pat. Nos. 3,072,676 and 3,201,416 ethylene monothiocarbonates may be prepared by a two-step-process. In a first step mercaptoethanol and chloro carboxylates are reacted to give hydroxyethylthiocarbonate, which is heated in the second step in a presence of metal salt catalyst to the ethylene monothiocarbonate.

According U.S. Pat. No. 3,517,029 alkylene monothiocarbonates are obtained by reacting mercaptoethanol and a carbonate diester in the presence of a catalytically active salt of thorium.

According to the process disclosed in U.S. Pat. No. 3,349,100 alkylene monothiocarbonates are obtained by reacting an epoxide with carbonylsulfide. The availability of carbonylsulfide is limited. Yields and selectivities of alkylene monothiocarbonates obtained are low.

A synthesis using phosgene as starting material is known from U.S. Pat. No. 2,828,318. Phosgene is reacted with hydroxymercaptanes. Yields of monothiocarbonates are still low and by products from polymerization are observed.

A preferred process for the preparation of the monothiocarbonate A), in particular of monothiocarbonates of formula I, is a process wherein a) a compound with one epoxy group (shortly referred to as epoxy compound) is used as starting material b) the compound is reacted with phosgene or an alkyl chloroformate thus giving an adduct and c) the adduct is reacted with a compound comprising anionic sulfur to give the monothiocarbonate A).

to the compound with one epoxy group a)

Preferably, the compound with one epoxy group is a low molecular weight compound with a molecular weight below 5000 g/mol, in particular below 1000 g/mol respectively below 500 g/mol. A compound with one epoxy group is, for example, epichlorhydrin, glycidol or a glycidylether or a glycidylester or propylenoxide.

To b) first process step, formation of adduct.

In the first process step the compound with one epoxy group is reacted with phosgene or an alkyl chloroformate thus giving an adduct. Preferably, it is reacted with phosgene. The word phosgene shall include any phosgene substitutes; phosgene substitutes are compounds that set free phosgene. A phosgene substitute is, for example, triphosgene. Below the reaction under b) is shown exemplarily for a specific epoxy compound substituted by R and phosgene as reactant.

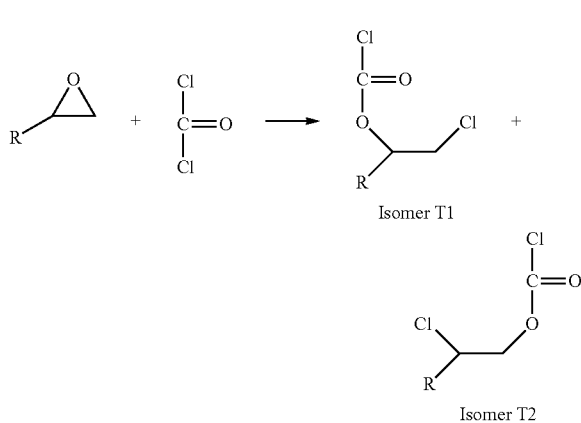

Isomer T1

Isomer T2

Two structural isomers of β-chloroalkyl chloroformate T1 and T2 are obtained. It is an advantage that the product has a high selectivity regarding the structural isomers. In particular, at least 80%, preferably at least 90% usually at least 95% of the adduct correspond to isomer T1.

The compound with one epoxy group may be reacted with phosgene or an alkyl chloroformate in any stochiometric ratio. Preferably, a very high excess of the compound with at least one epoxy group is avoided, as such a high excess would result in high amounts of unreacted starting compounds which would have to be removed during work-up of the obtained product composition.

Preferably, the phosgene, respectively chloroformate are used in an amount of 0.1 to 5 mol, in particular of 0.5 to 2 mol per mol of the epoxy group. In a particularly preferred embodiment the phosgene, respectively chloroformate, are used in excess.

With at least equimolar amounts of phosgene, respectively chloroformate, epoxy groups that remain unreacted can be avoided. Hence, in a preferred embodiment the phosgene, respectively chloroformate, are used in an amount of 0.9 to 5 mol, more preferably of 1 to 2 mol, in particular 1 to 1.5 mol per mol of the epoxy group.

The phosgene and the chloroformate are preferably a compound of formula II

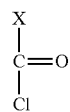

wherein X is Cl in case of phosgene or a group O—$R^9$ with $R^9$ representing a C1- to C4 alkyl group in case of chloroformate.

In a preferred embodiment the compound is reacted with phosgene.

Preferably, the reaction is performed in presence of a catalyst. Suitable catalysts are salts with a quaternary ammonium cation such as tetraalkylammonium halogenides, in particular chlorides, for example tetrabutylammoniumchloride, tetrahexylammoniumchloride, benzyltributylammonium chloride oder trioctylmethylammonium chloride.

Further suitable catalysts are, for example, hexa-alkylguanidinium halogenides, in particular chlorides, quarternary phosphonium halogenides, in particular chlorides, pyridine or other compounds with a ring system comprising nitrogen such as imidazole or alkylated imidazole.

Preferred catalysts are salts with a quaternary ammonium cation, in particular salts of tetra alkyl ammonium, for example tetra (n-butyl) ammonium chloride.

Preferably, the catalyst is used in an amount of 0.001 to 0.1 mol, in particular in an amount of 0.005 to 0.05 mol per mol of epoxy group.

The phosgene or alkyl chloroformate is preferably added to the compound with at least one epoxy group. As the reaction is exothermic, addition of phosgene or alkyl chloroformate is preferably made slowly so that the temperature of the reaction mixture is kept at the desired value. Preferably, the reaction mixture is cooled during the addition.

Preferably, the temperature of the reaction mixture is kept at −40 to 60° C., notably at 5 to 50° C.

Low molecular compounds with one epoxy group are usually liquid; hence, an additional solvent is not required. Preferably, a solvent is used in case that compounds are solid at 21° C. Suitable solvents are, in particular, aprotic solvents. Suitable solvents are, for example, hydrocarbons, including aromatic hydrocarbons and chlorinated hydrocarbon.

When the reaction is completed, unreacted phosgene or chloroformate may be removed from the mixture by distillation. No further work up is necessary.

The product mixture obtained comprises a compound with at least one β-chloro alkylchlorformate group. The next process step may follow immediately.

c) second process step, formation of the monothiocarbonate groups

Below the reaction under b) is exemplarily shown for a specific epoxy compound substituted by R and phosgene as reactant. Starting with the compound with the β-chloro alkylchlorformate group formed above, the second process step c) can be exemplarily shown for $Na_2S$ as reactant as follows:

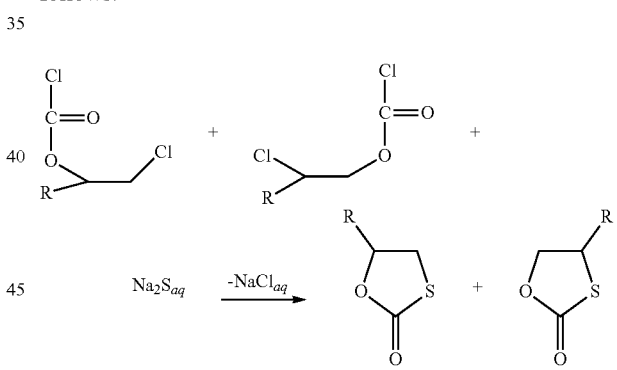

In this step the ratio of structural isomers T1 and T2 obtained in the first step and hence the selectivity is preserved.

Preferably, the product mixture obtained under b) is used under process step c) without any further work-up.

A solvent may be added in step c). Suitable solvents are, in particular, aprotic solvents. Suitable solvents are, for example, hydrocarbons, including aromatic hydrocarbons and chlorinated hydrocarbon or hydrophilic aprotic solvents, for example ethers such as tetrahydrofuran, dioxane, polyether such as glymes, acetonitrile or dimethylsulfoxid.

The product mixture from step b) is reacted with a compound comprising anionic sulfur.

The compound comprising anionic sulfur is preferably a salt.

The anionic sulfur is preferably $S^{2-}$, a polysulfide of formula $(S_p)^{2-}$ with p being an integral number from 2 to 200, preferably from 2 to 10 or $HS^{1-}$.

The cation of the salt may be any organic or inorganic cation. Preferably, it is an inorganic cation, in particular a metal. Usual metal cations are, for example, cations of alkali or earth alkali metals, such as sodium or potassium.

Preferred salts are Na$_2$S, K$_2$S, NaSH or KSH or any hydrates thereof.

The salt may be used in combination with a basic compound, notably a metal hydroxide, such as, in particular, NaOH or KOH. Such an additional basic compound is preferably used in case of salts with SH$^-$ as anion.

The anionic sulfur may also be generated in situ, starting from sulfur or a compound comprising sulfur in non-ionic form. For example, H$_2$S may be used as source for anionic sulfur. In presence of a basic compound, for example NaOH (see above), anionic sulfur is obtained from H$_2$S in situ.

The salt with anionic sulfur, respectively the compound from which anionic sulfur is generated in situ (together referred herein as the sulfur compound), is preferably added to the product mixture obtained in b). The sulfur compound may be added as such or, for example, as solution in a suitable solvent, such as water. In a preferred embodiment of the invention, the sulfur compound is dissolved in a solvent, in particular water, and the solution is added.

If the sulfur compound is added as solution in water, a two-phase system comprising an organic and an aqueous phase is obtained and the reaction occurs in such two-phase system. If a one phase system is desired instead, a suitable solvent may be added which acts as intermediary to combine the aqueous and organic phase to one phase again. A suitable solvent may be a hydrophilic aprotic solvent, for example a hydrophilic aprotic solvent listed above.

As the reaction is exothermic as well, addition of the salt, respectively the solution of the salt, is preferably made slowly so that the temperature of the reaction mixture is kept at the desired value. Preferably, the reaction mixture is cooled during the addition.

Preferably, the temperature of the reaction mixture is kept at −40 to 60° C., notably at −10 to 50° C.

Preferably, the salt is added in an amount of 0.5 to 2.0 mol per mol of the compound with the β-chloro alkylchlorformate group.

Preferably, the salt is added in an amount of 1.0 to 2.0 mol per mol of the compound with the β-chloro alkylchlorformate group.

In a most preferred embodiment, the salt is added in an amount of 1.0 to 1.3 mol per mol of the compound with at least one β-chloro alkylchlorformate group, as no significant excess of the salt is required to get a quick and complete reaction of all β-chloro alkylchlorformate groups.

By reaction with the salt the β-chloro alkylchlorformate group is transferred into the five-membered cyclic monothiocarbonate group, in particular the monothiocarbonate of formula I.

If desired, the second process step may be performed in the presence of a catalyst. Such a catalyst is, for example, a phase transfer catalyst such as ammonium salts, heterocyclic ammonium salts and phosphonium salts.

The final product obtained under c) may be worked up by extracting with a hydrophilic solvent, preferably water. In case that the above salt of anionic sulfur has been used in form an aqueous solution nor further water may be required. The organic and aqueous phase are separated. The organic phase may be washed with water which has preferably a pH of 4 to 10, in particular a pH of at least 7. The organic phase comprises the compound with at least one monothiocarbonate group. The aqueous phase comprises unreacted sulfide/hydrogensulfide salt and/or metal chloride (NaCl) and at least partially any catalyst added.

Any solvent may be removed from the organic phase by distillation. The obtained compound with at least one monothiocarbonate group may be further purified by distillation or may be used without further purification.

The process for the preparation of the preferred monothiocarbonate of formula I comprises a) an epoxy compound of formula III

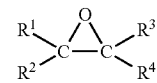

with R$^1$ to R$^4$ having the same meaning as in formula I as starting material, b) reacting the epoxy compound with the compound of formula II

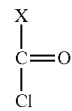

wherein X is Cl (phosgene) or a group O—R$^9$ with R$^9$ representing a C1- to C4 alkyl group (chloroformate) to give an adduct of formula IV

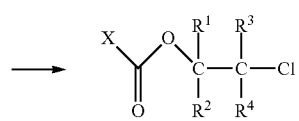

wherein R$^1$ to R$^4$ have the meaning above and c) reacting the adduct of formula IV with a compound comprising anionic sulfur to the monothiocarbonate of formula I

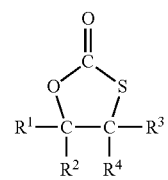

All disclosure in this patent application relating to process steps b) and c) apply to the above preparation of the preferred monothiocarbonate of formula I.

Compounds of formula I

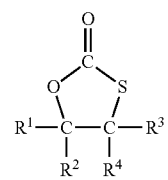

wherein two or three of R$^1$ to R$^4$ represent hydrogen and the groups R$^1$ to R$^4$ not being hydrogen represent a group CH$_2$—O—R$^5$ or —CH$_2$—O—C(=O)—R$^6$ or —CH$_2$—NR$^7$R$^8$ with R$^5$ to R$^8$ being an organic group with up to 30 carbon atoms have not been produced by processes of the prior art and are now accessible by the new process claimed hereunder.

To compound B)

Compound B) is a compound with at least two amino groups, selected from primary or secondary amino groups. In this patent application the word amino group shall mean a primary or secondary amino group if not indicated otherwise or obvious from the content otherwise.

Compound B) may have, for example, a molecular weight of up to 500.000 g/mol. The latter might be the case if compound B) is a high molecular compound such as a polymer comprising amino groups.

Preferred compounds B) have a molecular weight of up to 1000 g/mol. Most preferred are compounds B) having a molecular weight of from 60 g/mol to 500 g/mol.

Compounds B) may have, for example, up to 1000 amino groups, in particular up 500 and preferably up to 100 amino groups. A high number of amino groups which may be the case with polymeric compounds B) such as linear or branched polyvinylamine, polyethylenimine, polylysin or polypropylene imine.

In a preferred embodiment compound B) comprises 2 to 10 amino groups, preferably 2 or 3 amino groups and, in a most preferred embodiment compound B) comprises 2 amino groups.

In a preferred embodiment at least one of the amino groups is a primary amino group.

In a particularly preferred embodiment at least two of the amino groups are primary amino groups.

In a most preferred embodiment compound B) is a compound with two primary amino groups.

In a preferred embodiment compounds B) do not comprise any monothiocarbonate groups and do not comprise any functional groups which react with the group —SH as listed for compound C).

In a particularly preferred embodiment compounds B) do not comprise other functional groups than primary or secondary amino groups, carboxylic ester groups or ether groups.

Suitable compounds B) are for example

Alkylendiamines or alkylenpolyamines such as ethylenediamine, propylenediamine, butylene diamine, pentamethylene diamine, hexamethylene diamine, neopentanediamine, octamethylendiamine, 1,3 diaminopentane, 2-Methylpentan-1,5-diamin Alkylendiamines or alkylenpolyamines comprising ether groups (polyetheramine) such as such polyglycoldiamine, oxypropylene diamine or polyoxypropylene diamine.

Amino acids with two amino groups are, for example, lysin and ornithin.

Other diames are, for example, 4,7,10 Trioxatridecane-1,13-diamine, 4,9-dioxadodecane-1,12-diamine, 3,6-dioxa-1,8-octane diamine, 4,7-dioxa-1, 10-decanediamine, cycloaliphatic diamines, such as cyclohexyldiamines, for example 1,2 diaminocyclohexane, 1-methyl-2,4-diaminocyclohexane, 1-methyl-2,6-diaminocyclohexane or mixtures thereof, isophorone diamine, bis(4-amino-cyclohexyl)methane, 1,3-bis(aminomethyl)cyclohexane, 1,4-bis(aminomethyl)cyclohexane, 2,5-bisaminomethyl tetrahydrofuran, 3,3"-Dimethyl-4,4"diamino-dicyclohexylmethane aromatic diamines such as 1,2-phenylendiamine or 1,4 phenylendiamine, toluene diamines, 4,4' diamino-diphenylmethane, 4,4' diaminodiphenylsulfone, 2,5-bisaminomethyl furan, amino compounds with primary and secondary amino groups such as N-aminoethylpiperazine, dialkylentriamines or polyalkylentriamines, for example diethylenetriamine or triethylenetetramine, dipropylene triamine, N,N-Bis-(3-aminopropyl)methylamine, fatty diamines Further compounds B) with more than two amino groups are for, example Polyimin, polyvinylamin, polyallylamine, polylysine, polyetheramines based on TMP, Di-TMP, glycerol, pentaerythrit, polyglyerol, glucosamine, epoxy-amines (from molar excess of diaminocompounds+epoxy resin), 3-(2-Aminoethyl)-1,5-pentanediamine, 3,3',3"-Triamino-tripropylamine, polyamidoamines, aminoalkyl melamine, amino functionalized inorganic hybrid materials such as e.g. metal organic frameworks.

Compounds B may also be used in a form wherein the amino groups are protected with a protecting group. As soon as it become necessary or desired the protecting group is removed so that the compounds B) above with free amino groups are obtained. Usually, removal of the protecting groups occurs under the conditions of the reaction. Usual protected amino groups for amino groups are, for example, ketamine, aldimine, imidazolidine, oxazolidine, lewis acid complexed amines, carbamates, benzyloxycarbonyl amines, acyloximes, formanilidine. The deprotecting reaction can, for example, be triggered by either temperature, light, pH or presence of water/humidity.

To compound C)

Compound C) comprises at least two functional groups that reacts with a group —SH or, in case of a carbon-carbon triple bond as functional group that react with a group —SH, compound C) comprises at least one carbon-carbon triple bond.

A carbon-carbon triple bond may react twice with —SH. In a first reaction, an —SH group may undergo an addition reaction to the triple bond whereby the triple bond becomes a double bond. The double bond formed may react with a further group —SH. Hence one triple bond is equivalent to two other functional groups that react with a group —SH.

Compound C) may have, for example, a molecular weight of up to 500.000 g/mol. The latter might be the case if compound C) is a high molecular compound such as a polymer comprising functional groups that react with a group —SH.

Preferred compounds C) have a molecular weight of up to 1000 g/mol. Most preferred are compounds C) having a molecular weight of from 60 g/mol to 500 g/mol.

Compounds C) may have, for example, up to 1000 functional groups that react with a group —SH, in particular up 500 and preferably up to 100 functional groups that react with a group —SH.

In a preferred embodiment compound C) comprises 2 to 10 functional groups that react with a group —SH, however, in case of carbon-carbon triple bonds as unsaturated group, preferred compound C) comprise 1 to 5 triple bonds.

In a most preferred embodiment compound C) comprises 2 or 3 functional groups that react with a group —SH, however in case of triple bonds as unsaturated group, most preferred compound C) comprise 1 or 2 triple bonds.

In a preferred embodiment compounds C) do not comprise primary or secondary amino groups and do not comprise monothiocarbonate groups.

In a particularly preferred embodiment compounds C) do not comprise other functional groups than functional groups selected from the functional groups which react with the group —SH, carboxylic ester groups or ether groups.

In a preferred embodiment, the reaction of the functional group of compound C) with the group —SH results in the formation of a sulfur-carbon bond.

The reaction of the functional group of C) with the group —SH may be an addition reaction, a condensation reaction or a nucleophilic substitution reaction.

Compounds C), that undergo an addition reaction with the group —SH are, for example, compounds with ethylenically unsaturated groups selected from non-aromatic carbon-carbon double bonds or carbon-carbon triple bonds, or compounds with epoxy groups or compounds with isocyanate groups as functional groups.

Compounds C), that undergo a condensation reaction with the group —SH are, for example, compound with carbonyl groups as functional group, for example dicarbonyl compounds such as dialdehydes or diketones.

Compounds C), that undergo a nucleophilic substitution reaction with the group —SH are, for example, compounds with an halogenide, in particular chloride, as functional group, for example dihalogenides preferably dichlorides.

Preferably, the functional groups of compound C) that react with —SH are selected from non-aromatic, ethylenically unsaturated groups, epoxy groups, isocyanate groups, groups with a nonaromatic carbon-nitrogen double bond, carbonyl groups or halogenids. Non-aromatic, ethylenically unsaturated groups are non-aromatic carbon-carbon double bonds or carbon-carbon triple bonds.

More preferably, the functional groups of compound C) that react with —SH are selected from ethylenically unsaturated groups or epoxy groups.

Most preferably, the functional groups of compound C) that react with —SH are ethylenically unsaturated groups.

In one particularly preferred embodiment of the invention, the functional groups of compound C) that react with —SH groups are methacryl groups.

In one embodiment of the invention epoxy groups are excluded as functional groups of compound C) that react with —SH.

To compounds C) with ethylenically unsaturated groups as functional groups.

Compounds C) with unsaturated groups selected from non-aromatic carbon-carbon double bonds or carbon-carbon triple bonds are preferably polymerizable by a radical, cationic or an anionic polymerization mechanism.

In a preferred embodiment the unsaturated groups of compound C) are non-aromatic carbon-carbon double bonds.

Preferred compounds C) comprise 2 to 10, in particular 2 or 3 unsaturated groups, in case of triple bonds as unsaturated group, preferred compound C) comprise 1 to 5, in particular 1 or 2 triple bonds.

Compounds C with triple bonds are, for example alkynes, such as acetylene or propyne, mixtures of propyne/allene or propargyl alcohol, ethers of propargyl alcohol. or esters of propargyl alcohol.

Preferred compounds C) are those wherein the carbon-carbon double bond is a vinyl group $CH_2=CH—$; a vinylene group $—CH=CH—$, an unsaturated carbonyl group $CH_2=CR—C(=O)—$ with R=H, alkyl; an acryl group $CH_2=CH—C(=O)—O—$; a methacryl group $CH_2=C(CH_3)—C(=O)—O$, an acrylamide group $CH_2=CH— C(=O)—N$, or a cyanacryl-group $CH_2=C(CN)— C(=O)—O$, or an methylenmalonate-group $CH_2=C[—C(=O)—O]_2$ or an vinylene 1,3 dicarbonyl group $CH_2=C[—C(=O)—]_2$ or an allyl group $CH_2=CH—CH_2—$, especially allylethers $CH_2=CH—CH_2—O—$ or an maleimide group.

In the following the term "(meth)acryl" is used. The term "(meth)acryl" denominates an acryl group or methacryl group and a (meth) acryl compound is a compound comprising acryl groups or methacryl groups or both.

Preferred compound C) are in particular compounds with at least two acrylic or methacrylic groups, at least two vinyl groups or olefines with at least two carbon-carbon double bonds, unsaturated polyesters or cyanaurates or isocyanurates which are substituted by at least two unsaturated groups.

Olefines with two carbon-carbon double bonds are, for example, butadiene, cyclooctadiene, cyclododecatriene, isoprene, limonene, divinyl cyclohexane or poybutadiene or polyisoprene.

Compound C) with at least two acrylic or methacrylic groups are in particular (meth)acrylic esters of polyfunctional alcohols or of alkoxylated polyfunctional alcohols.

Examples of such alcohols are bifunctional alcohols, such as ethylene glycol, diethylene glycol, triethylene glycol, propylene glycol, dipropylene glycol, tripropylene glycol, butanediol, pentanediol, hexanediol, neopentyl glycol, alkoxylated phenolic compounds, such as ethoxylated or propoxylated bisphenols, cyclohexanedimethanol, trifunctional and higher-functional alcohols, such as glycerol, trimethylolpropane, butanetriol, trimethylolethane, pentaerythritol, ditrimethylolpropane, dipentaerythritol, sorbitol, mannitol and the corresponding alkoxylated, in particular ethoxylated and propoxylated, alcohols.

(Meth)acrylic esters of polyesterols may also be mentioned as oligomers.

Suitable polyesterols are, for example, those which can be prepared by esterification of polycarboxylic acids, preferably dicarboxylic acids, with polyols, preferably diols. The starting materials for such polyesters containing hydroxyl groups are known to the person skilled in the art. Preferably used dicarboxylic acids are succinic acid, glutaric acid, adipic acid, sebacic acid, o-phthalic acid, the isomers and hydrogenation products thereof and esterifiable derivatives, such as anhydrides or dialkyl esters of said acids. Maleic acid, fumaric acid, tetrahydrophthalic acid or the anhydrides thereof are also suitable. Suitable polyols are the above mentioned alcohols, preferably ethylene glycol, 1,2- and 1,3-propylene glycol, butane-1,4-diol, hexane-1,6-diol, neopentyl glycol, cyclohexanedimethanol and polyglycols of the ethylene glycol and propylene glycol type.

(Meth)acrylates of polyesterols can be prepared in a plurality of stages or in one stage, as described, for example, in EP 279 303, from acrylic acid, polycarboxylic acid and polyol.

Epoxide (meth)acrylates or urethane (meth)acrylates may also be suitable oligomers.

Epoxide (meth)acrylates are, for example, those which are obtainable by reacting epoxidized olefins or poly- or mono- or diglycidyl ethers, such as bisphenol A diglycidyl ether, with (meth)acrylic acid.

The reaction is known to the person skilled in the art and is described, for example, in R. Holmann, U. V. and E. B. Curing Formulation for Printing Inks and Paints, London 1984.

Urethane (meth)acrylates are in particular reaction products of hydroxyalkyl (meth)acrylates with poly- or diisocyanates (cf. also R. Holmann, U. V. and E. B. Curing Formulation for Printing Inks and Paints, London 1984).

Further oligomers are, for example, low molecular weight unsaturated polyesters which in particular have double bonds as a result of a content of maleic acid or fumaric acid or itaconic acid.

Oligomers with at least two vinyl groups are, for example divinylether such as diethylenglycol- or triethylenglycol-divinylether.

Further oligomers are, for example divinyl sulfon, or

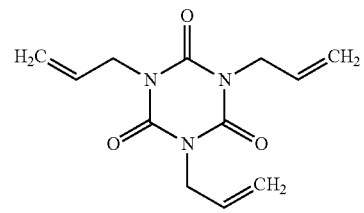
triallyl isocyanurate

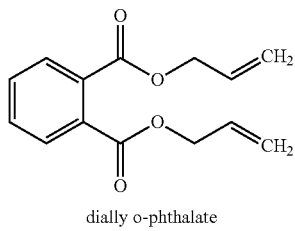
dially o-phthalate

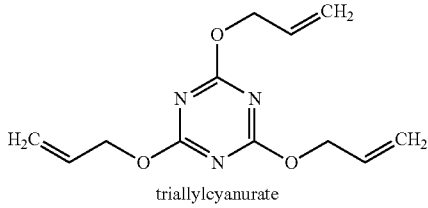
triallylcyanurate

In a preferred embodiment, compounds C) with ethylenically unsaturated groups as —SH reactive groups are acrylic or methacrylic compounds, in particular (meth)acrylates of polyfunctional alcohols, or compounds with vinylether groups or unsaturated polyester. In a particularly preferred embodiment, compounds C) with ethylenically unsaturated groups as —SH reactive groups are methacrylic compounds.

To compounds C) with epoxy groups as functional groups

Compounds C) with at least two epoxy groups are for example, compounds obtained by reacting the compounds with at least two alcohol groups with epichlorohydrin. Examples which may be mentioned are the diglycidyl ethers of bisphenol A or bisphenol F or bisphenol S and the diglycidylethers of hydrogenated bisphenol A or bisphenol F or diglycidylethers of aliphatic diols such diglycidylethers of polyalkoxylene diols. Mentioned may be also oligoglycidylether based on oligoalcohols. Examples are also epoxy resins which are obtainable by using the compounds with at least two alcohol groups in excess compared to the epichlorhydrin. In such epoxy resins the degree of polymerization of the compound with at least two alcohol groups is preferably from 2 to 25, in particular from 2 to 10.

Further examples are epoxidized fatty acid, fatty acid ester or fatty acid alcohol which have at least two epoxy groups.

Other compounds with at least two epoxy groups are, for example, tetraglycidylmethylenedianiline (TGMDA), triglycidylaminophenol and triglycidylisocyanurate, see below

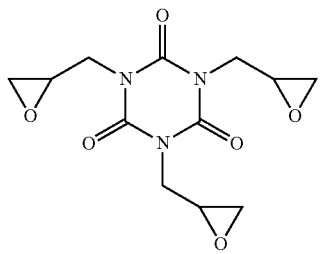 [SMILES: O=c1n(CC2CO2)c(=O)n(CC2CO2)c(=O)n1CC1CO1]

Other compounds C) with more than one epoxy group may be obtained by polymerization or copolymerization of glycidyl (meth)acrylate or of glycidyl vinylether.

To compounds C) with isocyanate groups as functional groups

Compounds C) with isocyanate groups as functional groups are diisocyanates and polyisocyanates with at least three isocyanate groups.

Diisocyanates or polyisocyanates may be aliphatic, cycloaliphatic or aromatic compounds.

Diisocyanates are, for example, 2,2"-, 2,4"- and 4,4"-diphenylmethane diisocyanate, isophoron diisocyanate, 2,4- or 2,6-toluylen diisocyanate (TDI), tetramethylen diisocyanate, hexamethylene diisocyanate (HDI), naphtylen diisocyanate or uretdiones of diisocyanates.

Polyisocyanates are, for example, isocyanurates of diisocyanates.

Diisocyanates or polyisocyanate may also be prepolymers obtained by reacting the above di- and polyisocyanates with polyols having at least two hydroxy groups or polyamines having at least two amino groups selected from primary or secondary amino groups.

To compounds C) with different functional groups Compound C) may have different functional groups that react with —SH, for example one epoxy group and one (meth)acryl group. Such compounds are, for example, vinyl (meth)acrylate, allyl (meth)acrylate, glycidyl (meth)acrylate or allyl glycidyl ether or polymeric compounds comprising different functional groups.

To compound D) with at least one primary or secondary amino group and at least one functional group that reacts with a group —SH Compound D) is a compound with at least one amino group and at least one functional group that reacts with a group —SH. The functional group that react with —SH are the same groups as mentioned regarding compound C).

Compound D) may have, for example, a molecular weight of up to 500.000 g/mol. The latter might be the case if compound D) is a high molecular compound such as a polymer comprising at least one primary or secondary amino group and at least one functional group that react with a group —SH.

Preferred compounds D) have a molecular weight of up to 1000 g/mol. Most preferred are compounds D) having a molecular weight of up to 500 g/mol.

In compound D), the number of primary or secondary amino groups and functional groups that react with a group —SH may be in total up to 1000, respectively 500, preferably 100. A high number of amino groups which may be the case with polymeric compounds D).

In a preferred embodiment compound D) comprises in total one to three primary or secondary amino groups, preferably one or two primary or secondary amino groups and, in a most preferred embodiment compound D) comprises one amino group, only.

In a preferred embodiment compound D) comprises at least one primary amino group.

In a particularly preferred embodiment compound D) comprises one amino group, only and the amino group is a primary amino group.

In a preferred embodiment compound D) comprises in total one to three functional groups that react with a group —SH. In a more preferred embodiment compound D) comprises one or two functional groups that react with a group —SH. In a most preferred embodiment compound D) comprises one functional groups that react with a group —SH, only.

The functional group of compound D) that reacts with a group —SH is preferably a non-aromatic carbon-carbon double bond or triple bond.

In a preferred embodiment compounds D) do not comprise monothiocarbonate groups.

In a particularly preferred embodiment compounds D) do not comprise other functional groups than functional groups selected from the functional groups which react with the group —SH, primary or secondary amino groups or carboxylic ester groups or ether groups.

In a particularly preferred embodiment compound D) is a compound with one primary amino group and one group reactive with —SH, which is in particular a non-aromatic carbon-carbon double bond.

In a most preferred embodiment compound D) is a compound with one primary amino group and one non-aromatic carbon-carbon double bond and does not comprise any other functional groups.

Suitable compounds D) are for example aminopropyl amine vinyl ether and allyl amine, see formulas below

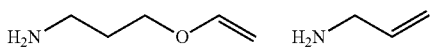

To the first alternative of the synthesis of the polymer with urethane groups.

The principles of the reaction of A) with B) and C) are as follows:

The ring of the thiocarbonate A) is opened by reaction of A) with an amino group of compound B). As B) has two amino groups the reaction occurs twice. Product of the ring-opening reaction is a compound with urethane groups, herein referred to as intermediate.

This ring-opening reaction is exemplarily shown below for a specific compound A) and B).

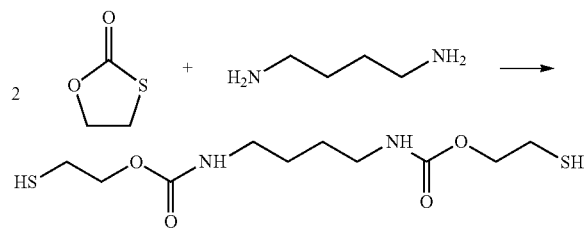

In the above example an intermediate is formed with two thiol groups —SH and two urethane groups.

The —SH group is highly reactive and readily reacts with the reactive groups of compound C) as described above.

The reaction of the intermediate with two SH groups with a compound C) having two reactive groups is a polymerization reaction and results in the formation of a polymer having urethan groups.

Hence, a polymer with urethane groups is obtainable by the process of this invention. This polymer typically comprises structural elements of formula V

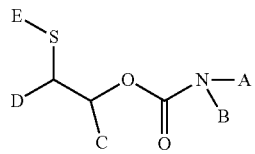

The variables A to E represent substitutions by any substituents.

The typical structural element is a urethane group with a sulfur atom being bonded via an ethylene group to the oxygen of the urethane group.

A polymer with urethane groups is obtainable by the process, regardless whether the reaction is carried out in one step or two steps. The polymer comprises the urethane groups in form of the structural element of formula V.

Preferably, the polymer obtainable by the process has a content of structural elements of formula V of 0.0001 to 0.3 mol, notably of 0.001 to 0.2 mol per 100 g of polymer, whereby the structural element of formula V is calculated to have a molecular weight of 3×12+2×16+14+32=114 g/mol, which is the sum of the molecular weight of all atoms C, O, N and S in formula V.

The reaction of the first alternative is preferably carried out in one step by reacting A), B) and C) simultaneously or in two steps by first reacting A) with B) and then reacting the obtained intermediate with C).

The stoichiometry of the two-step synthesis is as follows:

Two mols of compound A) react with two mol amino groups of compound B) and the obtained intermediate with two mol —SH groups reacts with two mol of reactive groups of compound C). As both B) and C) may have 2 or more than 2 reactive groups the resulting stoichiometric molar relationship of monothiocarbonate groups to amino groups and to reactive groups of compound C) is x mol A:x/n mol B:x/m mol C, wherein x is an integral number, n is the number of primary and secondary amino groups of compound B and m is the number of reactive groups of compound C). In a preferred embodiment x, n and m independently from one another are 1, 2 or 3. The above molar relationship does apply to compounds C) with triple bonds as well, however, one triple bond is equivalent to two double bonds as reactive group.

Preferably, a large excess of any compound is avoided and any of compounds A) B) and C) are used in an amount that deviates not more than 50%, respectively not more than 20% from the equimolar amounts corresponding to the stoichiometry of the reactions.

The compounds A), B) and C) may also be reacted simultaneously in one step (hereinafter referred to as one-step reaction). The result of the one-step reaction depends on the nature of compound C), as reactive groups of compound C) may also react with the amino groups of compound B) thus reducing the availability amino groups for the ring-opening reaction, see above. It has to be distinguished between following cases:

Case 1

If the reactivity of compound A) with the amino groups of B) is much higher than the reactivity of compound C) with the amino groups, the result of the one-step reaction of A), B), and C) corresponds to the result of the two-step reaction as A) and B) will react first, followed by the reaction of the obtained intermediate with C).

Case 2

If the reactivity of compound A) and C) with the amino groups is in the same order of magnitude, a one-step reaction of A), B), and C) will result in a hybrid polymer comprising urethane groups.

Case 3

In case that the reactivity of compound A) with the amino groups of B) is much lower than the reactivity of compound C) with the amino groups, the result of the one-step reaction of A), B), and C) is a polymer with low amount of urethane groups.

The further disclosure relates to specific compounds C):

To the synthesis with compounds C) having at least two epoxy groups

This may often be a Case 2, depending on the reactivity pattern of the starting materials employed. The reactivity of epoxy groups of C) with amino groups of B) is often similar to the reactivity of compound A) with the amino groups of B). In the one-step reaction of all three components, there will be competing reactions of the amino groups of compound B) with either compound A) (ring-opening of the monothiocarbonate) or compound C) (crosslinking/chain extension of epoxy compounds with amino compounds). As product of this one-step reaction a hybrid polymer is obtained. The molar ratio of compounds A) to C) determines the nature of the hybrid polymer. With minor amounts of compound A) the hybrid polymer obtained corresponds to an epoxy resin which is modified with urethane groups. The obtained urethane-modified epoxy resins have improved application properties and combines the benefits of epoxy resins with those resulting from the content of urethane groups.

Hence, it is an embodiment of the invention, to react A), B) and C) whereby C) is a compound with at least two epoxy groups in one step. Preferably, the molar ratio of compounds A) to the moles of epoxy groups of C) is from 1:100 to 100:1. More preferred is a ratio compounds A) to the moles of epoxy groups of C) of 50:1 to 1:50. Employing a highly reactive thiocarbonate derivative such as the unsubstituted cyclic monothiocarbonate the reaction pathway can be shifted to follow Case 1.

Preferably, compounds C) with at least two epoxy groups as functional groups are reacted with A) and B) following the two-step synthesis by first reacting compound A) with B) and then reacting the obtained intermediate with compound C) as described above.

To the synthesis with compounds C) having at least two methacrylic groups as unsaturated groups These systems usually follow Case 1 since aza-Michael addition of amines towards methacrylates are considered unfavorable while addition of mercaptanes can proceed at low temperature. Such behavior is described in (Polymer preprints 2010, 51, 281)

To the synthesis with compounds C) having at least two acrylic groups as unsaturated groups These systems usually follow Case 3.

It is known in literature that aza-Michael addition reaction with acrylates can be suppressed under certain reaction conditions (solvent dependence). Depending on the resulting kinetics of the aza-Michael addition the overall system can subsequently follow Case 2 or even Case 1.

To the synthesis with compounds C) having other unsaturated groups which are non-activated double bonds, such as vinyl ethers or olefins.

These systems usually follow Case 1. Addition of —SH to the unsaturated group of compound C can preferably be achieved via radical reaction. Radical reaction can be thermally catalyzed and/or photoinitiated.

To the synthesis with compounds C) having at least two isocyanate groups as unsaturated groups This is a Case 3. Therefore, a one-step reaction is not preferred.

General issues of the process

Compounds A), B) and C) may be mixed to obtain a curable mixture comprising

A) a five-membered cyclic monothiocarbonate

B) a compound with at least least two amino groups, selected from primary or secondary amino groups and C) a compound which at least two functional groups that reacts with a group —SH or, in case of a triple bond as functional group that react with a group —SH, with at least one triple bond In case of the two-step reaction a curable mixture is prepared for the second step comprising the reaction product of the two components A) and B) and, in addition, C).

For storage compounds A), B) and C) may be kept separately. It is possible to combine component A) and C) and keep B) separately, resulting in a two components curable system comprising a first component of A) and C) and a second component B).

Preferably, the reaction of A), B) and C) is performed at temperatures of from −20 to 250° C., preferably between 20 and 100° C. This applies to the one step reaction and to both steps of the two-step reaction. Alternatively, any activation energy for the reactions may be provided by high-energy radiation such as visible or UV-light.

The one-step or two-step reaction may be performed with solvent. The use of a solvent might be helpful, in case that at least one of the compounds A), B) and C) is solid and other liquid compounds A), B) or C) do not act already as solvent for the solid compound. Suitable solvents are, for example, ethylacetate, butylacetate, methyl ethyl ketone, dioxane, methanol, ethanol, water, tetrahydrofuran and dimethylformamide. It is an advantage of the process that usually no additional solvent is required as usually at least one of the compounds A), B) and C) is liquid and serves already as solvent.

Furthermore, the above composition of A), B) and C) or the separate compositions in case of a two component curable systems may comprise further additives, for example catalysts or inhibitors or additives which are necessary or desired for the intended use of the polymer obtained.

Catalysts may, for example, be used in case of compounds C) that add via an addition reaction to the groups —SH. Addition reactions may follow an ionic or a radical mechanism. The ionic mechanism usually requires the presence of a basic compound as catalyst. The basic catalyst may be compound B) itself. In case of an addition to ethylenically unsaturated groups the presence of compound B) is often sufficient. In case of epoxy groups as functional groups preferably a basic catalyst such as a tertiary amine, for example Versamin® is added. Such catalysts are usually used in an amount of 0.1 to 3 mol catalyst per one mol of epoxy groups. Other catalysts may be amidine or guanidine based systems or phosphines A radical mechanism of the addition reaction is supported by initiators that form radicals. Such initiators are either thermal or photoactive initiators well known from radical polymerization.

Furthermore, the above composition of A), B) and C) or the separate compositions in case of a two component curable systems may comprise stabilizers. Such stabilizers might be helpful to avoid decomposition or early polymerization in case of long time storage or transport of the compositions.

In particular, redox stabilizers that reduce or avoid oxidation of S—H groups which is a side reaction may be added. Oxidation of S—H groups may lead to disulfide bridges between neighbored molecules thus reducing the amount of S—H groups available for the reaction with compound C. An example of such stabilizer is Tris(2-carboxyethyl) phosphin (TCEP).

Alternatively, any additives or stabilizers may also be added after the reaction to the polymer obtained.

In the above reactions, further compounds, notably compounds with only one amino group or compounds with only one functional group that reacts with a groups —SH, other than a triple bond may, be used. Such compounds would act as modifier which limits the molecular weight of the polymer obtained. In a preferred embodiment, the polymer obtained by the process of this invention consists to at least 60% notably to at least 80% by weight of compounds A), B) and C). In a more preferred embodiment the polymer obtained by the process of this invention consists to at least 90% notably to at least 95%, respectively to at least 98% by weight of compounds A), B) and C).

The obtained polymers are usually transparent, non-tacky and solid at room temperature.

To the second alternative of the synthesis of the polymer with urethane groups.

The polymer of the second alternative is obtained by reacting compounds A) and D). In case of reacting A) and D) a ring-opening of the monothiocarbonate by an amino group of D) and formation of a urethane group occurs first. The obtained intermediate has a group —SH and at least a functional group reactive with —SH. This intermediate can polymerize and build a polymer chain by reaction of the —SH group of one molecule with the functional group of another molecule.

According to the stoichiometry of the reaction one mol of monothiocarbonate A) requires one mol of amino groups of compound D) to have full conversion of all monothiocarbonates. Each monothiocarbonate produces one group —SH via ring opening; hence one mol of functional group of compound D) reacts with one mol of groups —SH under formation of a polymer. Compounds A) or D) may be used in excess. Any excess of either compound A) or D) has an impact on the molecular weight of the obtained polymer. Preferably a large excess of any compound is avoided and compounds A) and D) are used in an amount that deviates not more than 50%, respectively not more than 20% from the equimolar amounts corresponding to the stoichiometry of the reactions. In a most preferred embodiment equimolar amounts corresponding to the stoichiometry of the reactions are used.

The disclosure above relating to the performance of the reaction of A), B) and C) and the use of additives, stabilizers and catalysts applies also to reaction of compound A) and D). In particular, all disclosure relating to functional groups that are reactive with a group —SH which has been made above with regard to compound C) shall relate to compound D) as well.

A polymer with urethane groups is obtainable by the process according to the second alternative as well. The polymer comprises the urethane groups in form of the structural element of formula V in the same amounts as already described above in case of the first alternative.

The polymer obtained from A) and D) are usually colorless solid at room temperature and nontacky.

The process of this invention provides an alternative method for the manufacturing of polymers with urethane groups. In this process the use of compounds with isocyanate groups is avoided. The process of this invention is an easy and effective manufacturing process, notably a process not requiring high energy or high temperatures. Solid and transparent polymers are easily available and are useful for a variety of technical applications such as coatings, adhesives, thermoplastic or duroplastic material for the formation of molds in any form. Hybrid polymers are available with modified properties due to the introduction of urethane groups in polymers such as epoxy resins. Optical polymers with high refractive index are accessible. Polymers obtained show high thermal stability. The process furthermore offers a curing mechanism for low temperature curing which is compatible with the presence of oxygen.

EXAMPLES

Following compounds with one five-membered cyclic monothiocarbonate group have been used in the examples:

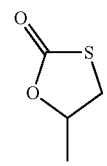

methyl mono thiocarbonate (MTC)

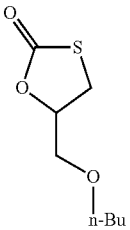

n-butylglycidyl-mono thiocarbonate (BTC)

Synthesis of the Cyclic Monothiocarbonates

First Step

The epoxide listed in Table 1 was charged to a reactor and kept at −30° C. The molar amount of epoxide is listed in Table 1 as well. 0.01 mol of tetra(n-butyl ammonium chloride were added per 1 mol of epoxide. Thereafter phosgene is added slowly as the reaction is exothermic. When adding the phosgene the temperature was kept via cooling below 20° C. The total amount of phosgene was 1.1 mol per 1 mol of epoxide. When the addition of phosgene was completed the reaction mixture was further stirred for about (2 hours). Unreacted phosgene was removed by nitrogen stripping. No further work-up was necessary. The obtained •-chloro alkylchlorformates could be used directly in the next step which is the formation of the thiocarbonates. The epoxide, the obtained β-chloro alkylchlorformates and further details of the reaction are listed in Table 1.

Second Step

The respective β-chloroalkyl chloroformate (50 g) and dichloromethane (50 mL) are placed in a 500 mL 4 neck round bottom flask equipped with a KPG crescent stirrer, dropping funnel, thermometer and a reflux condenser. The solution was cooled down to 0° C. with an ice bath before $Na_2S$ (1 equiv., 15 wt % aqueous solution) was slowly added, maintaining the temperature at 5° C. After the complete addition the ice bath was removed and the reaction mixture allowed to warm to room temperature. After stirring for 4 h the phases were separated and the aqueous phase was extracted with dichloromethane (2×50 mL). The solvent was removed from the combined organic phases under reduced pressure and the residual liquid purified by (Kugelrohr) distillation, yielding the desired cyclic thiocarbonate.

TABLE 1

| epoxide | •-chloro al-kylchlorformates | Yield Of •-chloro al-kylchlorformates (%) | Mono-thiocarbonate | Yield of monothio-carbonate (%) |
|---|---|---|---|---|
|  (1,6 mol) | 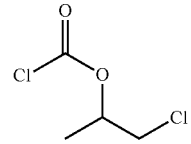 | >99 | 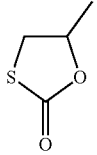 | 84 |
|  (1,0 mol) | 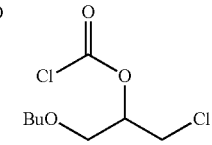 | 96 | 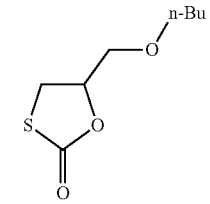 | 92 |

Preparation of Polymers

Example 1

Polymer of Methyl Monothiocarbonate, Diamine and Compound C with Double Bond

In a flask fitted with a mechanical stirrer methyl monothiocarbonat (3.00160 g, 0,025405 mol) was combined with 1,4-Butandiol dimethacrylat (95%, 3.00981 g, 0.0127 mol) and 5 mg tris(2-carboxyethyl)phosphin (TCEP) which is a redox-stabiliser and the mixture was subsequently homogenized. The flask was purged with nitrogen. To the solution was added 1,5-Pentandiamin (1.29922 g, 0.0127 mol, 1 eq.) via syringe. The reaction mixture was stirred gently under N2 atmosphere at T=60° C.

The reaction scheme is as follows:

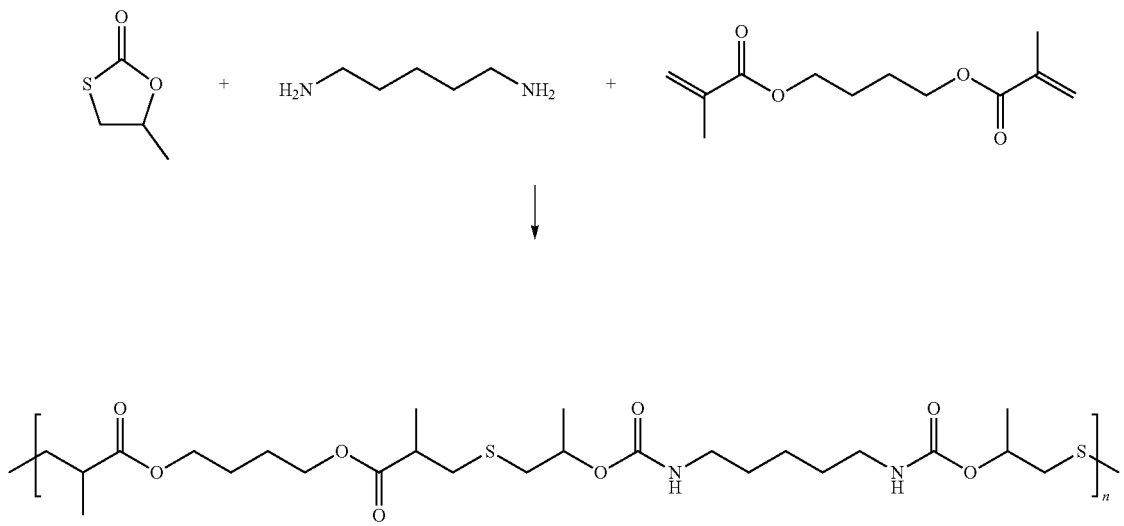

After 22 h a colorless and transparent polymer was obtained. Thermogravimetric experiments (air atmosphere) demonstrated high thermal stability with observed degradation at 280-300° C.

Thermal stability was characterized by Decomposition Temperature (Td) via Thermogravimetric Analysis (TGA) (air, 10 K min$^{-1}$, 50-650° C.);

|  | Td [° C.] |
|---|---|
| Example 1 | 300 |

Example 2

Polymer of n-Butylglycidyl-Monothiocarbonate, Diamine and Compound C with Double Bond In a flask fitted with a magnetic stirrer n-butylglycidyl-thiocarbonate (5.0 g, 0.026 mol, 1 eq) was combined with trimethylolpropane-trimethacrylat, ((technical grade, 2.97 g, ⅓ eq.) and subsequently homogenized. To the solution was added 1,5-pentandiamine (1.34 g) rapidly. After 10 second of vigerous stirring at room temperature, the reaction mixture was poured in metal mold (bar-shaped), volume 10 ml each). The molds were stored at 60° C. for 12 hours and the samples were subsequently released from the molds. The polymer was obtained as a colorless solid bar with high transparency. The polymer showed high thermal stability.

Thermal stability was characterized by Decomposition Temperature (Td) via Thermogravimetric Analysis (TGA) (air, 10 K min$^{-1}$, 50-650° C.);

|  | Td [° C.] |
|---|---|
| Example 2 | 285 |

The reaction scheme is as follows:

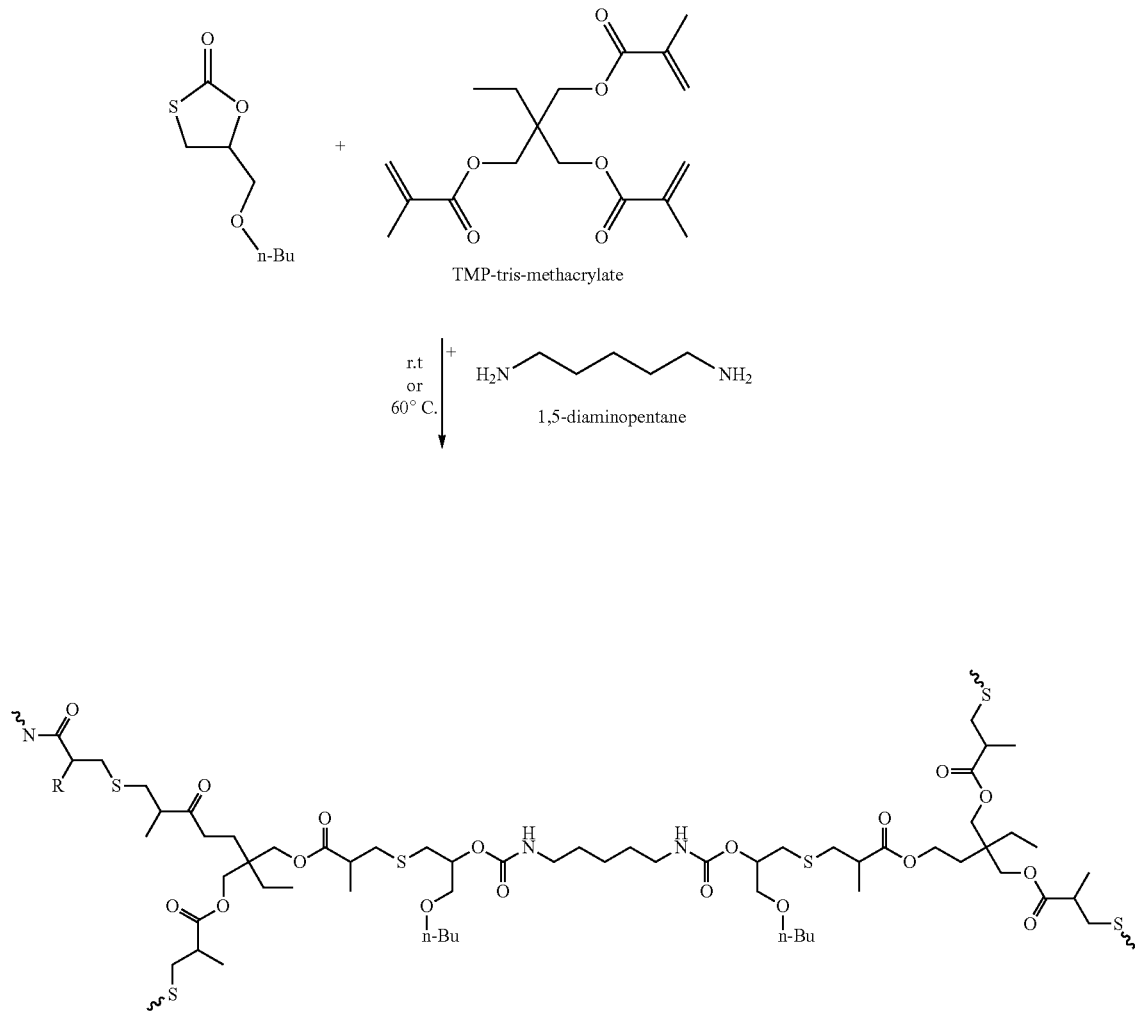

Example 3

Polymer of Methyl Monothiocarbonate, Methylcyclohexanediamine (MCDA) and Compound C with Epoxy Group Epilox A19-03 resin (297.48 g) which is Bisphenol A diglycidylether obtained from Leuna Harze GmbH was placed in a container. Vacuum was applied to remove air bubbles (speed mixer). 38.83 g of n-butylglycidyl-monothiocarbonate and methylcyclohexane diamine (MCDA, 52.04 g) were added, stirring (2000 rpm) as continued for 1 minute. The catalyst Versamin® EH50 (11.66 g) was added and mixing was continued for 1 min. (1000 rpm). Vacuum was applied to remove air bubbles. The reaction mixture was subsequently poured into a mold (approx. 32×22 cm) and was cured at 80° C. for 3h.

The reaction scheme is as follows:

Example 4

Polymer of n-Butylglycidyl Monothiocarbonate, Diamine (Polyetherdiamine) and Compound C with Epoxy Group Epilox® A19-03 (266.14 g) which is Bisphenol A diglycidylether obtained from Leuna Harze GmbH was placed in a container. Vacuum was applied to remove air bubbles (speed mixer). 38.83 g of n-butylglycidyl-mono thiocarbonate and Jeffamine D230 (83.38 g), which is a polyetherdiamine were added, stirring (2000 rpm) as continued for 1 minute. A catalyst (Versamid® EH50, 11.65 g which is a tertiary amine) was added and mixing was continued for 1 min. (1000 rpm). Vacuum was applied to remove air bubbles. The reaction mixture was subsequently poured into a mold (approx. 32×22 cm) and was cured at 80° C. for 3h.

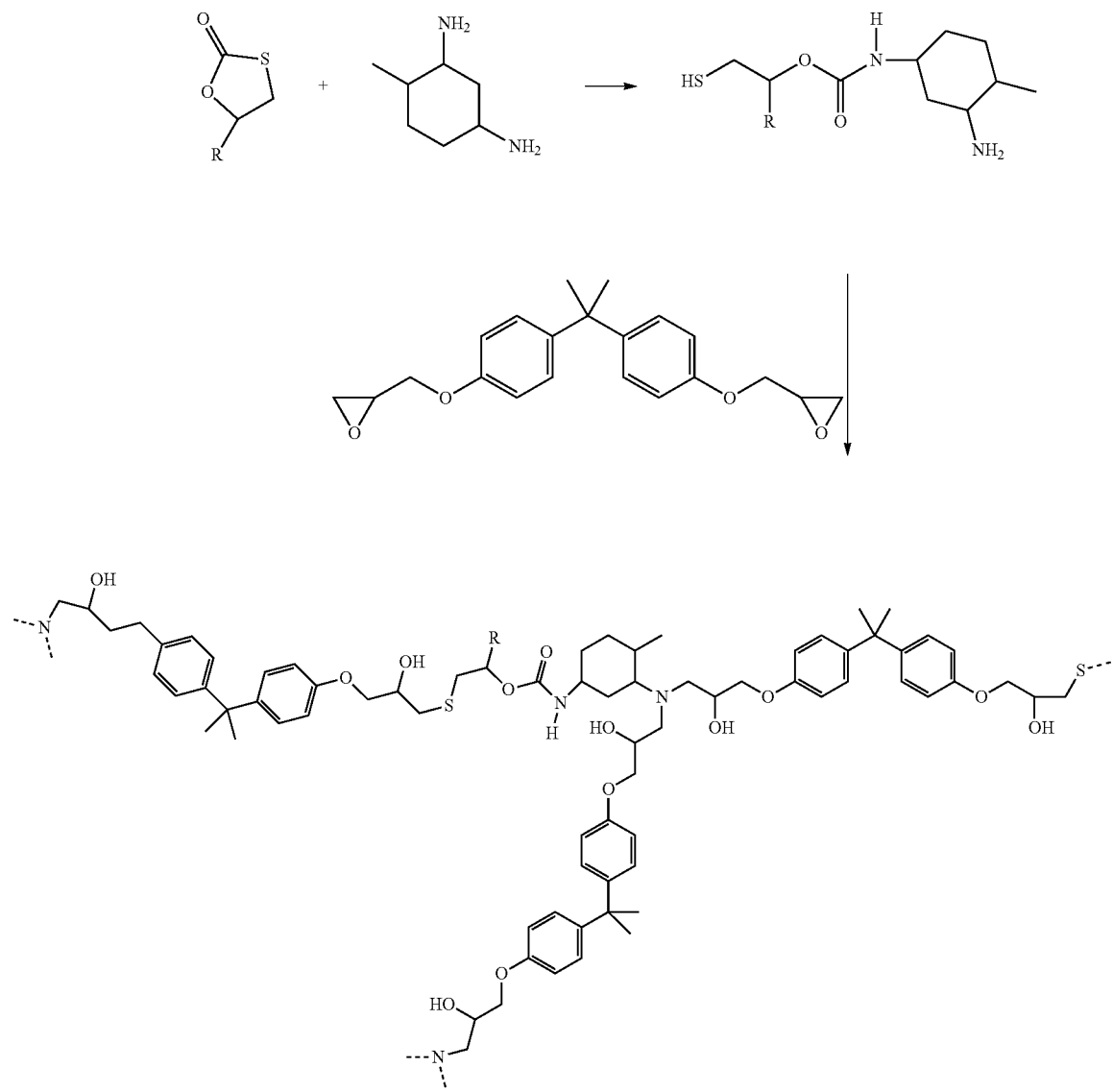

The polymer obtained was solid and transparent. In the mold the compounds had cured to a solid, transparent panel.

The polymer obtained was solid and colourless. In the mold the compounds had cured to a solid transparent panel.

Comparison Example 1

Example 4 has been repeated without monothiocarbonate. Hence the reaction taking place is the well-known cross-linking of epoxy compounds with amines, only.

Epilox A19-03 (266.14 g) was placed in a container. Vacuum was applied to remove air bubbles (speed mixer). Jeffamine® D230 (83.38 g) was added, stirring (2000 rpm) as continued for 1 minute. A catalyst (Versamid® EH50, 11.65 g which is a tertiary amine) was added and mixing was continued for 1 min. (1000 rpm). Vacuum was applied to remove air bubbles. The reaction mixture was subsequently poured into a mold (approx. 32×22 cm) and was cured at 80° C. for 3h.

The polymer obtained was solid and yellowish. In the mold the compounds had cured to a solid yellowish panel.

Examples 5 to 10 and Comparison Examples 2 and 3

Polymer of Monothiocarbonate, Diamine and Compound C with Epoxy Group

All reactions were carried out in a DSC apparatus starting at 25° C. The energy profile of the reaction was followed in the DSC by applying a temperature ramp of 5K/min up to 200° C. The sample was subsequently kept isothermal for 10 minutes. The sample was then cooled down to −50° C. (ramp: 20° C./min) and subsequently kept isothermal for 15 minutes. Onset temperature, which corresponds to the beginning of the reaction, the exothermic temperatures corresponding to the maxima(s) of the exothermic peak(s) and the enthalpy determined are listed in the tables.

To determine the Tg of the polymer obtained the sample was reheated to 200° C. (ramp: 20K/min).

Example 5

Epoxy resin Epilox A19-03 (0.685 g) was added to the DSC sample pan. Buthoxy-substituted monothiocarbonate (0.1 g) was added followed by addition of Jeffamine D230 (0.215 g). After addition of the catalyst (Versamin® EH50, 0.028 g) the sample pan was placed into the DCS chamber at 25° C.

Examples 6 to 10 and Comparison Examples 2 and 3

In the further examples the compositions of example 5 have been varied, for example Jeffamine has been replaced by MCDA and n-butylglycidyl-mono thiocarbonate (BTC) has been replaced by methyl monothiocarbonate (MTC). In each example and comparison examples 8 parts by weight of Versamin EH50 per 100 parts by weight of the sum of all other components were added.

For all polymers the results show only moderate decrease in Tg in presence of monothiocarbonates compared with the pure epoxy resin obtained from epoxy compound and diamine.

The compositions and the results of all examples with Jeffamine D230 as diamine are found in Table 1

The compositions and the results of all examples with MCDA as diamine are found in Table 2.

All % in Table 1 and 2 are weight %.

TABLE 1

| | Comparison example 2 | Example 5 | Example 6 | Example 7 | example 8 |
|---|---|---|---|---|---|
| Epilox A19-03 (%) | 76.2 | 68.5 | 57.1 | 68.5 | 57.1 |
| Jeffamine D230 (%) | 23.8 | 21.5 | 17.9 | 21.5 | 17.9 |
| BTC (%) | | 10 | 25 | | |
| MTC (%) | | | | 10 | 25 |
| Exothermic Temperature (° C.) | 113.0 | 108.1 | 109.2 and 142.9 | 112.54 and 140.5 | 107.9 and 143.9 |
| Onset Temperature (° C.) | 79.2 | 73.5 | 72.5 | 74.1 | 70.7 |
| Enthalpy (J/g) | 439.9 | 402.4 | 257.5 | 390.5 | 279.8 |
| Tg (° C.) | 70.7 | 60.1 | 56.57 | 70.8 | 69.5 |

TABLE 2

| | Comparison example 3 | Example 9 | Example 10 |
|---|---|---|---|
| Epilox A19-03 (%) | 85.1 | 63.8 | 63.8 |
| MCDA (%) | 14.9 | 11.2 | 11.2 |
| BTC (%) | | 25 | |
| MTC (%) | | | 25 |
| Exothermic Temperature (° C.) | 104.3 | 105.2 | 101.8 and 146.8 |
| Onset Temperature (° C.) | 76.8 | 67.9 | 65.9 |
| Enthalpy (J/g) | 477.8 | 382.4 | 326.6 |
| Tg (° C.) | 112.9 | 85.1 | 97.2 |

Determination of Reactivity

The reactivity of the systems was determined by rheology measurements. Formulations were reacted at 70° C. in a rheometer (MCR 302, Anton Paar), equipped with a parallel plate system The time required to reach a viscosity of 10 Pa*s as well as well as the Gel Time was determined for comparison example 2 and example 5.

| | Time to reach 10 Pa*s [s] | Gel time [min] |
|---|---|---|
| Comparison example 2 | 53.3 | 89.1 |
| Example 5 | 29.1 | 81 |

The data reflect the increased reactivity in case of example containing cyclic monothiocarbonate.

Mechanical Performance

The mechanical performance of the samples was tested via determination of the Maximum Storage Modulus and the Compliance of the cured sample. A high value of compliance corresponds to good elastic properties.

| | Maximum Storage Modulus [Pa] | Compliance (μPa-1) |
|---|---|---|
| Comparison example 2 | 8.1 | 0.48 |
| Example 5 | 9.0 | 1.2 |

The data demonstrate that the urethan/epoxy hybrid material does not suffer from decreased storage modulus the same time showing significantly increased compliance.

Example 11

Polymer of Methyl-1,3-Oxathiolan-2-One, Diamine and Compound C with Double Bond

In a 50 ml flask fitted with a magnetic stirrer 5-Methyl-1,3-oxathiolan-2-one (8.86 g) was combined with trimethylolpropane-trimethacrylat, (8.46 g) and subsequently homogenized. To the solution was rapidly added 2,2'-(ethylenedioxy)bis(ethylamine) (5.56 g). The mixture was stirred and homogenized at room temperature.

The temperature of the mixture and the viscosity of the mixture increased over time and the sample was thoroughly cured after 20h (transparent polymer).

Example 12

Polymer of n-Butylglycidyl-Monothiocarbonate, Triamine and Compound C with Double Bond In a 50 ml flask fitted with a magnetic stirrer 5-(buthoxymethyl)-1,3-oxathiolan-2-one (5.71 g) was combined with trimethylolpropane-trimethacrylat, (3.38 g) and subsequently homogenized. To the solution was rapidly added tris(2-aminoethyl)amine (1.46 g). The mixture was stirred and homogenized at room temperature.

The viscosity of the mixture doubled within approx. 10 min; the sample was thoroughly cured after 20h (transparent polymer).

The invention claimed is:
1. A process for manufacturing a polymer comprising urethane groups, the process comprising:
in a first alternative, reacting
A) a five-membered cyclic monothiocarbonate, and
B) a compound comprising at least two amino groups, selected from primary or secondary amino groups, and
C) a compound comprising at least one carbon-carbon triple bond or at least two functional groups that react with a —SH group; or
in a second alternative, reacting
A) a five-membered cyclic monothiocarbonate, and
D) a compound with at least one primary or secondary amnmo group and at least one functional group that reacts with a group —SH,
wherein
A) is a monothiocarbonate of formula I

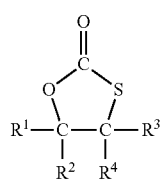

(I)

wherein $R^1$, $R^2$, $R^3$, and $R^4$ each independently represent hydrogen or an organic group comprising up to 50 carbon atoms; and $R^2$ and $R^4$ and the two carbon atoms to which $R^2$ and $R^4$ are bonded optionally form a five to ten membered carbon ring,
where in the first alternative when the at least two functional groups of compound C) that react with the —SH group are present they are selected from the group consisting of non-aromatic, ethylenically unsaturated groups, isocyanate groups, groups with a non-aromatic carbon-nitrogen double bond, carbonyl groups and halides, and
where in the second alternative, the compound D) includes as the at least one functional group a functional group selected from the group consisting of non-aromatic, ethylenically unsaturated groups; a carbon-carbon triple bond; isocyanate groups; groups with a non-aromatic carbon-nitrogen double bond; carbonyl groups; and halides.

2. The process of claim 1, comprising the first alternative, wherein B) is a compound comprising at least two aliphatic or cycloaliphatic primary amino groups.

3. The process of claim 1, comprising the first alternative, wherein the at least two functional groups of compound C) that react with the —SH group are present and are selected from non-aromatic, ethylenically unsaturated groups.

4. The process of claim 1, comprising the first alternative, wherein the at least two functional groups of compound C) that react with the —SH group are present and are methacryl groups.

5. The process of claim 1, comprising the first alternative, wherein the reacting of the first alternative comprises:
reacting A), B), and C) simultaneously; or
reacting A) with B), to obtain an intermediate, and then reacting the intermediate with C).

6. The process of claim 1, comprising the second alternative, wherein D) is a compound comprising one primary amino group and one non-aromatic carbon-carbon double bond or triple bond.

7. A polymer comprising urethane groups, wherein the polymer comprising the urethane groups is produced according to the process of claim 1.

8. A curable composition, comprising:
A) a five-membered cyclic monothiocarbonate,
B) a compound comprising at least two amino groups, selected from primary or secondary amino groups, and
C) a compound comprising at least one carbon-carbon triple bond or at least two functional groups that react with a —SH group; selected from the group consisting of non-aromatic, ethylenically unsaturated groups, isocyanate groups, groups with a non-aromatic carbon-nitrogen double bond, carbonyl groups and halides, or
a reaction product of A) and B), and C),
wherein
A) is a monothiocarbonate of formula I

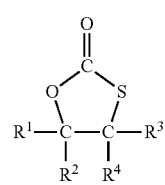

(I)

wherein $R^1$, $R^2$, $R^3$, and $R^4$ each independently represent hydrogen or an organic group comprising up to 50 carbon atoms, and
$R^2$ and $R^4$ and the two carbon atoms to which $R^2$ and $R^4$ are bonded optionally form a five to ten membered carbon ring.

9. A two-component curable system, comprising; a first component of A) and C) and a second component B), wherein
A) is a five-membered cyclic monothiocarbonate,
B) is a compound comprising at least two amino groups, selected from primary or secondary amino groups, and
C) is a compound comprising at least one carbon-carbon triple bond or at least two functional groups that react with a —SH group, selected from the group consisting of non-aromatic, ethylenically unsaturated groups, isocyanate groups, groups with a non-aromatic carbon-nitrogen double bond, carbonyl groups and halides
wherein
A) is a monothiocarbonate of formula I

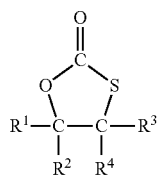

(I)

wherein $R^1$, $R^2$, $R^3$, and $R^4$ each independently represent hydrogen or an organic group comprising up to 50 carbon atoms, and
$R^2$ and $R^4$ and the two carbon atoms to which $R^2$ and $R^4$ are bonded optionally form a five to ten membered carbon ring.

10. A monothiocarbonate, which satisfies the following formula I,

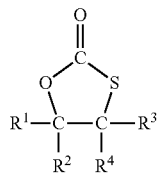

(I)

wherein $R^2$, $R^3$, and $R^4$ each represent hydrogen and $R^1$ is $CH_2$—O—$R^5$ or —$CH_2$—O—C(=O)—$R^6$, wherein $R^5$ and $R^6$ are each independently a C1 to C14 alkyl group.

11. The process of claim 1, wherein $R^1$ is selected from the group consisting of —$CH_2$—O—$R^5$, —$CH_2$—O—C(=O)—$R^6$, and —$CH_2$—$NR^7R^8$, and $R^5$ to $R^8$ is an organic group with up to 30 carbon atoms.

12. The process of claim 1, wherein $R^1$ is selected from the group consisting of $CH_2$—O—$R^5$ and —$CH_2$—O—C(=O)—$R^6$, wherein $R^5$ and $R^6$ are each independently a $C_1$ to $C_{14}$ alkyl group.

13. A polymer according to claim 7, wherein $R^1$ is selected from the group consisting of $CH_2$—O—$R^5$ and —$CH_2$—O—C(=O)—$R^6$, wherein $R^5$ and $R^6$ are each independently a $C_1$ to $C_{14}$ alkyl group.

14. A curable composition according to claim 8, wherein $R^1$ is selected from the group consisting of $CH_2$—O—$R^5$ and —$CH_2$—O—C(=O)—$R^6$, wherein $R^5$ and $R^6$ are each independently a $C_1$ to $C_{14}$ alkyl group.

15. A two-component curable system according to claim 9, wherein $R^1$ is selected from the group consisting of $CH_2$—O—$R^5$ and —$CH_2$—O—C(=O)—$R^6$, wherein $R^5$ and $R^6$ are each independently a $C_1$ to $C_{14}$ alkyl group.

16. The process of claim 1, comprising the first alternative, wherein the compound C) includes at least two functional groups that react with the —SH group that are selected from the group consisting of non-aromatic, ethylenically unsaturated groups; isocyanate groups; groups with a non-aromatic carbon-nitrogen double bond; carbonyl groups; and halides.

17. The process of claim 1, comprising the second alternative, wherein the compound D) includes as the at least one function group a functional group selected from the group consisting of non-aromatic, ethylenically unsaturated groups; isocyanate groups; groups with a non-aromatic carbon-nitrogen double bond; carbonyl groups; and halides.

18. A curable composition according to claim 8, comprising a reaction product of A) and B), and C).

19. A curable composition according to claim 8, comprising A) and B), and C).

20. A curable composition according to claim 1, wherein $R^1$, $R^2$, $R^3$, and $R^4$ each represent hydrogen.

* * * * *